United States Patent [19]

Russell

[11] Patent Number: 5,489,280
[45] Date of Patent: Feb. 6, 1996

[54] SURGICAL PREPARATION SOLUTION APPLICATOR

[75] Inventor: Ryder L. Russell, Sugarcreek, Ohio

[73] Assignee: Zimmer, Inc., Warsaw, Ind.

[21] Appl. No.: 331,402

[22] Filed: Oct. 31, 1994

[51] Int. Cl.[6] .................................................. A61M 35/00
[52] U.S. Cl. .......................... 604/311; 604/289; 604/315; 15/322
[58] Field of Search ................................ 604/73, 74, 289, 604/310, 311, 313, 315; 401/145, 171, 187, 205, 206; 15/322

[56] References Cited

U.S. PATENT DOCUMENTS

| | | |
|---|---|---|
| Re. 28,405 | 5/1975 | Sollerud. |
| 3,331,090 | 7/1967 | Reiber et al. ............... 401/187 |
| 3,538,535 | 11/1970 | Ginsburgh et al. .......... 15/322 |
| 3,783,473 | 1/1974 | Engguist ..................... 15/322 |
| 5,301,387 | 4/1994 | Thomas et al. ............. 15/322 |
| 5,336,170 | 8/1994 | Selerno et al. ............. 604/24 |
| 5,428,863 | 7/1995 | Tchcsecu et al. ........... 15/322 |

FOREIGN PATENT DOCUMENTS

| | | | |
|---|---|---|---|
| 0149442 | 12/1978 | Japan ...................... | 604/313 |
| 1620109 | 1/1991 | U.S.S.R. ................... | 604/313 |

Primary Examiner—Randall L. Green
Assistant Examiner—Mark O. Polutta
Attorney, Agent, or Firm—Todd A. Dawson

[57] ABSTRACT

A fluid applicator 10 used to prepare a surgical site on a patient's skin is disclosed, which irrigates a surgical site and simultaneously collects excess irrigation fluids from the surgical site and returns the collected fluids to a fluid reservoir. Applicator 10 includes a disposable fluid reservoir 10 and a reusable motor assembly 50. Fluid reservoir 20 includes a sponge 48. Motor assembly 50 includes a motor 70 and a reciprocating diaphragm 80. Motor assembly 50 is connected to the open end of fluid reservoir 20 to enclose and seal a quantity of prep solution inside the fluid reservoir. Motor 70 reciprocates diaphragm 80 back and forth within fluid reservoir 20. The forward stroke of diaphragm 80 causes a positive pressure inside fluid reservoir 20, which displaces the irrigation fluid through a one way valve 30 and a spray nozzle 34 onto the surgical site. Excess irrigation fluid is absorbed by sponge 48 as applicator 10 is moved over the surgical site. The rearward stroke of diaphragm 80 causes a negative pressure inside fluid reservoir 20, which draws the irrigation fluid collected within sponge 48 into a manifold chamber 41 and returns the collected irrigation fluid to fluid reservoir 20 through a second one way valve 32.

4 Claims, 3 Drawing Sheets

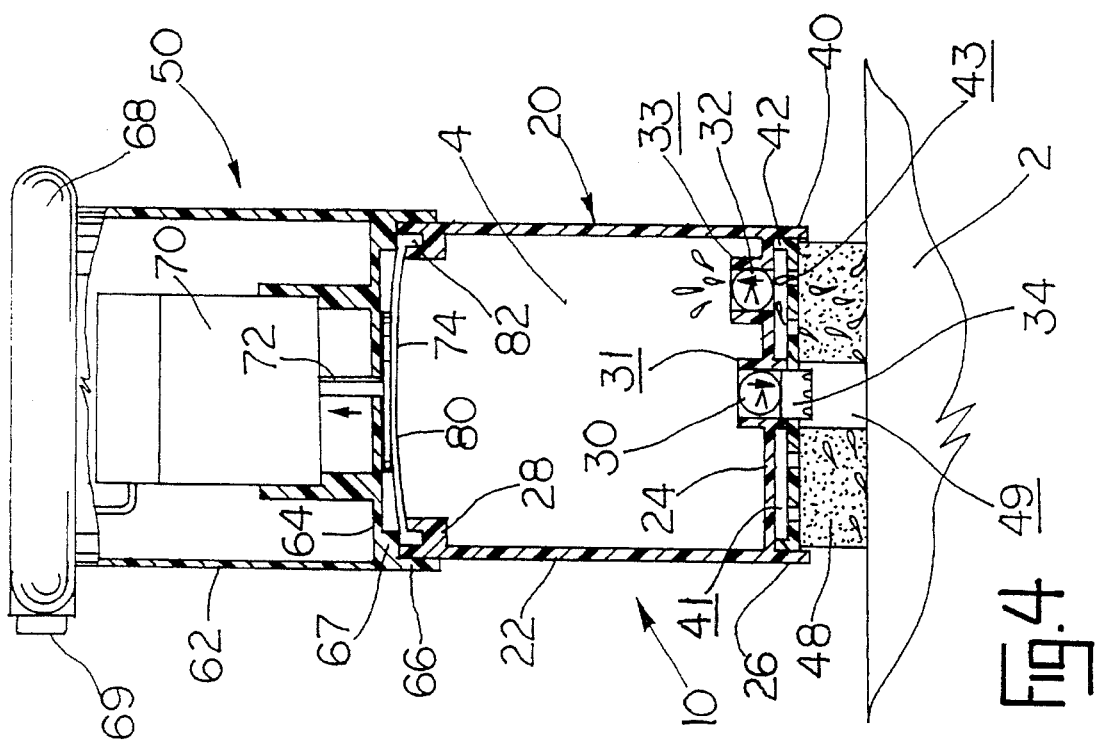
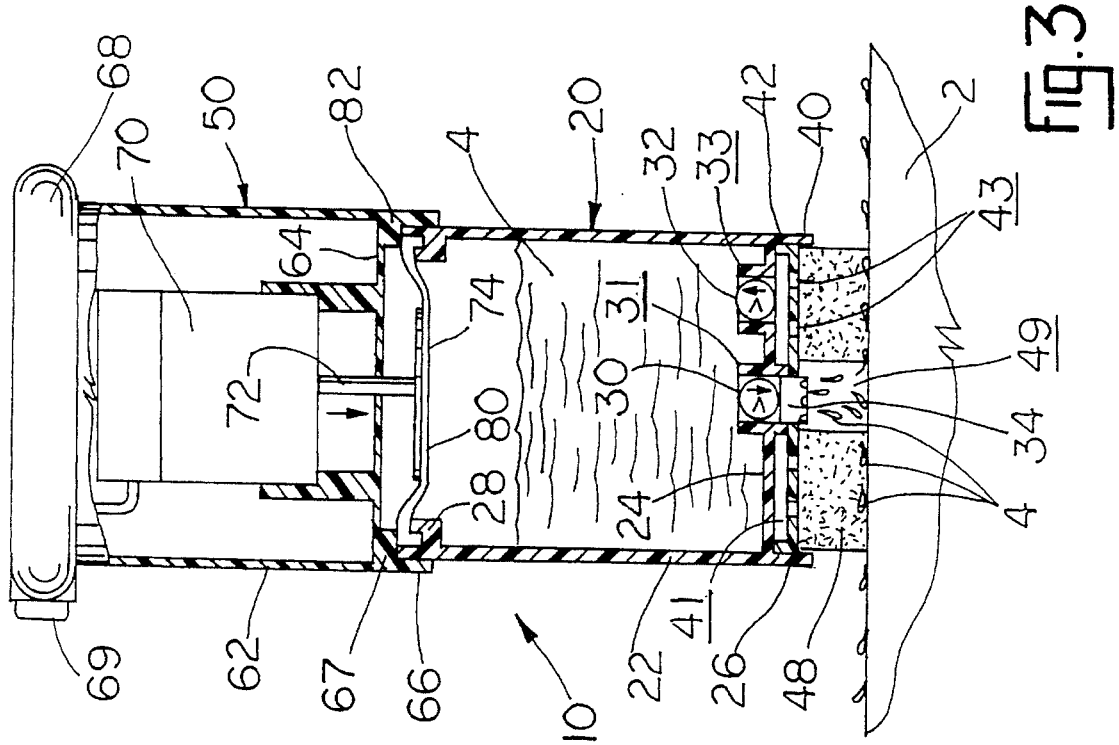

SURGICAL PREPARATION SOLUTION APPLICATOR

This invention relates to a fluid applicator and in particular, a fluid applicator used to prepare a surgical site on a patient's skin, which irrigates the surgical site with irrigation fluids and simultaneously collects excess fluids from the surgical site.

BACKGROUND OF THE INVENTION

The preparation and disinfection of the surgical site is critical for preventing infection, which is a primary concern in all surgical procedures. Disinfecting irrigation fluids, commonly referred to as prep solutions, are applied directly to the patient's skin to disinfect the surgical site. Typically, prep solutions include a varied mixture of betadine™, phisohex™, zephiran, lactated ringers, saline solution and other fluids. Each fluid component must be metered precisely to ensure the proper concentration and strength of the prep solution. Because prep solutions are inherently caustic, solutions that are mixed too strong can cause burns and skin irritation, while weak mixtures are less effective in disinfecting the surgical site.

Typically the prep solution is massaged into the skin using forceps and gauze pads. The massaging action in applying the solution ensures that solution is worked into the pores and fully irrigates the surgical area. This method of application is extremely messy. The excess solution can run under dressings and pool in body creases, which may result in chemical burns and skin irritation.

SUMMARY OF THE INVENTION

The fluid applicator of this invention irrigates the surgical site with prep solution and simultaneously collects excess fluid expelled from the fluid reservoir and returns it to the fluid reservoir. Since excess fluids used in the irrigation are collected and returned to the fluid reservoir, the applicator eliminates the medical concerns caused by fluid runs and drips over the patient's skin.

The applicator includes a disposable fluid reservoir and a reusable motor assembly. The fluid reservoir is marked to offer precise metering and mixing of the individual solution fluids inside the fluid reservoir. The fluid reservoir includes a sponge for collecting excess prep solution from the surgical site. The sponge also provides a soft surface for massaging the surgical site, which aids in working the prep solution into the patient's skin. The motor assembly includes an electric motor enclosed in a cylindrical housing and a reciprocating diaphragm. The motor assembly is connected to the open end of the fluid reservoir to enclose and seal a quantity of prep solution inside the fluid reservoir. The motor reciprocates the diaphragm back and forth within the fluid reservoir. The forward stroke of the diaphragm causes a positive pressure inside the fluid reservoir, which displaces prep solution through a one way valve and a spray nozzle onto the surgical site. Excess prep solution is absorbed by the sponge as the applicator is moved over the surgical site. The rearward stroke of the diaphragm causes a negative pressure inside the fluid reservoir, which draws prep solution collected within the sponge into a manifold chamber and returns the collected prep solution to the fluid reservoir through a second one way valve.

Accordingly, an advantage of this invention is to improve the preparation of a surgical site by providing a fluid applicator which reduces fluid drips and runs over the patient's skin.

Another advantage of this invention is to provide a fluid applicator which irrigates a surgical site with prep solution and simultaneously collects excess prep solution from the surgical site.

Another advantage of this invention is to provide a fluid applicator which can be used to accurately meter individual fluid components of the prep solution within the applicator.

Another advantage of this invention is to improve the preparation of a surgical site by providing a fluid applicator which can be used to massage the prep solution into the patient's skin.

Other advantages will become apparent upon a reading of the following description.

BRIEF DESCRIPTION OF THE DRAWINGS

A preferred embodiment of the invention has been depicted for illustrative purposes only wherein:

FIG. 3 is a sectional view of the prep solution applicator of this invention showing the back stroke of the diaphragm; and FIG. 4 is a sectional view of the prep solution applicator showing the forward stroke of the motor armature displacing the diaphragm to expel fluid from the fluid reservoir.

DESCRIPTION OF THE PREFERRED EMBODIMENT

The preferred embodiment herein described is not intended to be exhaustive or to limit the invention to the precise form disclosed. It is chosen and described to explain the principles of the invention and its application and practical use to enable others skilled in the art to utilize its teachings.

Figure 2:
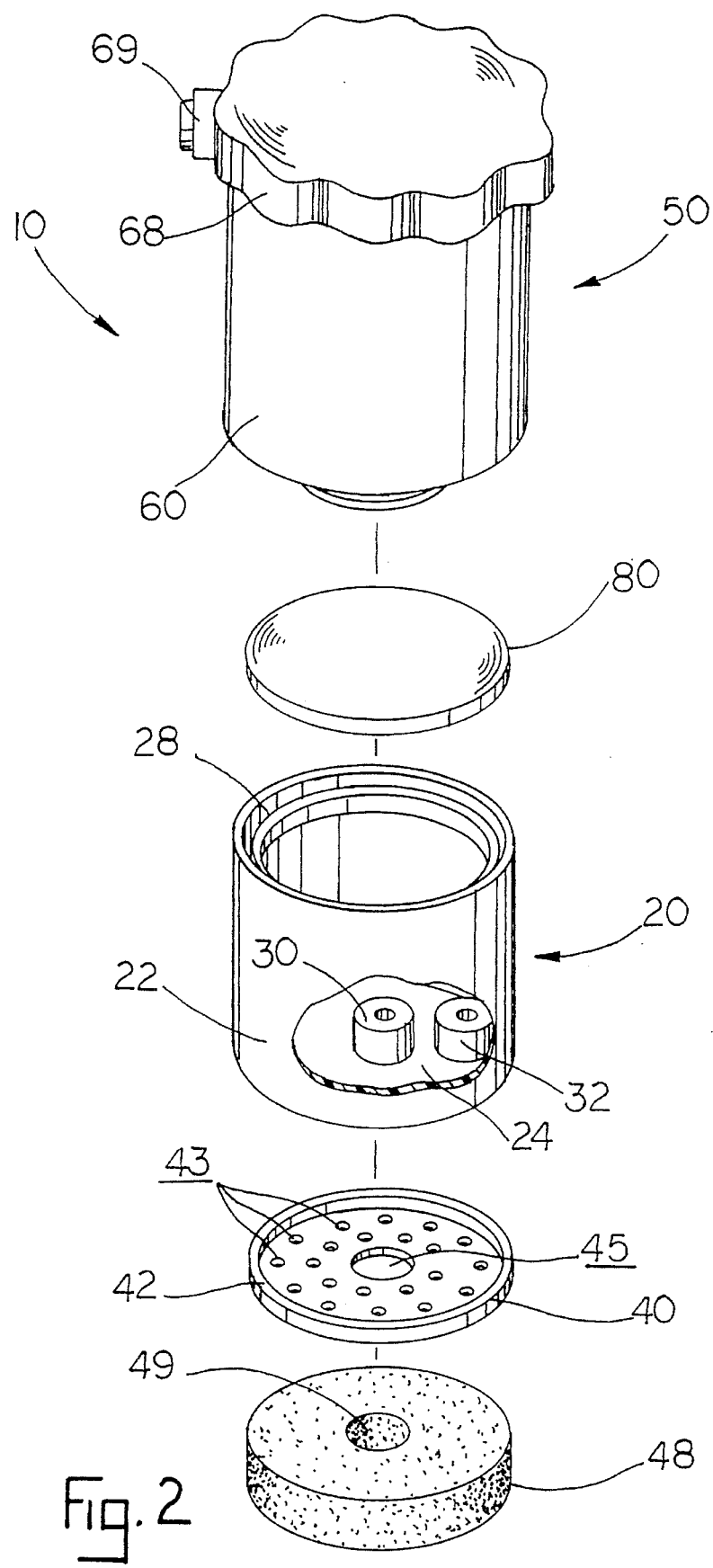
FIG. 2 is an exploded perspective view of the prep solution applicator of this invention showing the various internal components.

As shown in FIGS. 2–4, the fluid applicator 10 includes two separate units: a cylindrical fluid reservoir 20 and a motor assembly 50. Preferably, fluid reservoir 20 is designed as a disposable unit to be used only one time and sanitarily disposed of; however, the fluid reservoir can be modified to use individual components, which if desired can be cleaned, autoclaved and reused. In addition, fluid reservoir 20 can be pre-filled and prepackaged with a premixed prep solution for convenience. Preferably, motor assembly 50 is a reusable unit, which can be separately cleaned, sterilized and autoclaved.

As shown, fluid reservoir 20 has a cylindrical body and an open end defined by a side wall 22 and an inset distal end wall 24. Side wall 22 extends partially beyond end wall 24 to from an annular rim 26. An L-shaped flange 28 extends inwardly around the periphery of side wall 22 near its open end. Preferably, fluid reservoir 20 is constructed of a clear rigid plastic such as acrylic or ABS plastic and side walls 22 are marked to assist in the metering of solution fluids 4. End wall 24 has a central port 31 and a second off centered port 33. A one way valve 30 and a nozzle 34 are seated within a central port 31, which allow fluid to exit fluid reservoir 20. A second one way valve 32 is seated within port 33, which allows fluid to enter fluid reservoir 20. A manifold plate 40 is secured to the distal end of fluid reservoir 20 to define a manifold chamber 41. Manifold plate 40 includes a peripheral lip 42 and has a plurality of holes 43 spaced across its surface and a central opening 45. As shown, manifold plate 40 is seated within annular rim 26 of fluid reservoir 20. Nozzle 34 extends through manifold opening 45 and peripheral lip 42 spaces manifold plate 40 from end wall 24 to define a manifold chamber 41. A sponge 48 is secured to the outer face of manifold plate 40. Preferably, sponge 48 is secured to manifold plate 40 by an adhesive. Sponge 48 has a donut shaped body and a central opening 49. Nozzle 34 extends partially into sponge opening 49. Preferably, sponge 48 is constructed from an absorbent material which also has a texture conducive for massaging a prep solution into the skin.

Motor assembly 50 includes an electric motor 70 enclosed in a cylindrical housing 60 and a reciprocating external diaphragm 80. Motor housing 60 includes a cylindrical side wall 62 and an inset wall 64. Side wall 62 extends partially beyond end wall 64 to form an annular outer rim 66. Rim 66 includes an inner shoulder 67. Motor housing 60 also includes a hand grip 68 and an electrical switch for activating motor 69. Any conventional electrical motor can be used; however, a DC motor which uses a rechargeable battery pack is preferred. Motor 70 is mounted within housing 60 and includes a reciprocating drive shaft 72, which extends through end wall 64. The protruding end of shaft 72 terminates in a mounting plate 74. Diaphragm 80 is connected to mounting plate 74 by an adhesive. As shown, the diameter of diaphragm 80 is substantially equal to the inner diameter of fluid reservoir 20 and includes a peripheral lip 82. Preferably, diaphragm 80 is constructed of a butyl rubber or other suitable material.

In use, motor assembly 50 is connected to fluid reservoir 20 to enclose and seal a quantity of prep solution 4 inside fluid reservoir 20. Preferably, fluid reservoir 20 is filled with a pre-mixed prep solution. Alternatively, the individual solution fluids can be metered out and mixed directly within fluid reservoir 20. Motor housing 60 and fluid reservoir 20 are secured together by the complimentary engagement of housing rim 66 and reservoir side walls 22. Preferably, housing rim 66 is threaded onto reservoir side wall 22; but, any suitable method of connecting the motor housing to the fluid reservoir can be used. As shown in FIGS. 3 and 4, diaphragm lip 82 is restrictively seated between housing shoulder 67 and reservoir flange 28 to hermetically seal the prep solution within fluid reservoir 20.

When activated, motor 70 drives diaphragm 80 back and forth within fluid reservoir 20. The movement of diaphragm 80 creates positive and negative pressure within fluid reservoir 20. As shown in FIG. 3, the forward stroke of diaphragm 80 causes a positive pressure inside the fluid reservoir, which displaces prep solution through valve 30 and nozzle 34 onto the surgical site. Nozzle 34 expels prep solution directly onto the patient skin. Excess prep solution is absorbed by sponge 48 as applicator 2 is moved over the surgical site. As shown in FIG. 4, the rearward stroke of diaphragm 80 causes a negative pressure inside fluid reservoir 20, which draws prep solution collected within sponge 48 into manifold chamber 41 and returns the collected prep solution to fluid reservoir 20 through valve 32.

Figure 1:
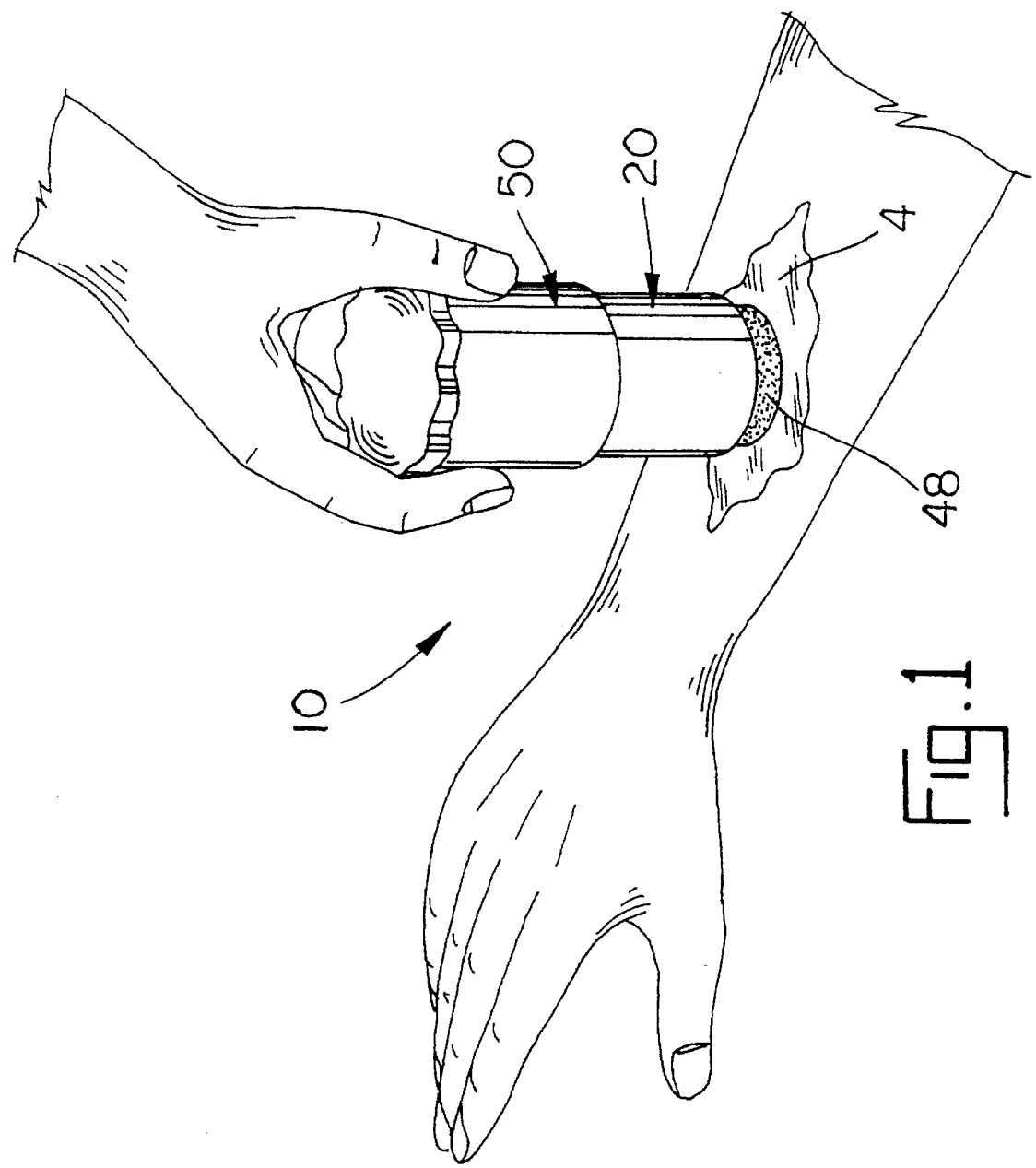
FIG. 1 is a perspective view of the prep solution applicator of this invention in use for preparing a surgical site on a patient's forearm.

As shown in FIG. 1, the operator moves applicator 10 back and forth over the surgical site. Applicator 10 irrigates the surgical site 2 with prep solution 4 and simultaneously collects excess prep solution from the surgical site and returns it to fluid reservoir 20. Sponge 48 provides a textured surface for massaging the patient's skin while the surgical site is irrigated. Light downward pressure applied during use of applicator 2 provides a massaging action to work the prep solution into the patient's skin. The natural vibrations produced by motor 70 aid the massaging action of applicator 2, which helps to work the prep solution into the patient's skin.

It is understood that the above description does not limit the invention to the details given, but may be modified within the scope of the following claims.

I claim:

1. A fluid applicator configured to massage and irrigate a surgical site on a patient's skin comprising:

a fluid reservoir for containing fluid configured to irrigate said surgical site, means connected to said fluid reservoir configured for collecting irrigation fluids from said surgical site, a motor assembly connected to said fluid reservoir, said motor assembly including means for expelling a fluid contained in said reservoir and adapted to irrigate said surgical site, said fluid reservoir includes a nozzle part for communicating said fluid from said fluid reservoir to said surgical site, said collecting means includes a sponge connected to said fluid reservoir, said sponge constituting means for engaging said surgical site when said applicator is used to massage and irrigate said surgical site, and means for returning fluids collected by said collecting means to said fluid reservoir.

2. The applicator of claim 1 wherein said motor assembly includes means for drawing collected fluid from said collecting means into said fluid reservoir.

3. The applicator of claim 1 wherein said motor assembly includes a diaphragm disposed within said fluid reservoir and means for reciprocating said diaphragm within said fluid reservoir to expel fluids from said fluid reservoir onto said surgical site and to draw collected fluids from said collecting means into said fluid reservoir.

4. The applicator of claim 1 wherein said returning means includes a manifold connected between said collecting means and said fluid reservoir for communicating collected fluids between said collecting means and said fluid reservoir.

\* \* \* \* \*